United States Patent [19]

Olson et al.

[11] Patent Number: 5,549,607
[45] Date of Patent: Aug. 27, 1996

[54] APPARATUS FOR SPINAL FIXATION SYSTEM

[75] Inventors: Carlton D. Olson, Los Angeles; Mark G. Urbanski, Indian Wells, both of Calif.

[73] Assignee: Alphatec Manufacturing, Inc., Palm Desert, Calif.

[21] Appl. No.: 397,717

[22] Filed: Mar. 2, 1995

Related U.S. Application Data

[63] Continuation of Ser. No. 20,288, Feb. 19, 1993, abandoned.

[51] Int. Cl.$^6$ .................................................. A61B 17/70
[52] U.S. Cl. ............................................. 606/61; 606/73
[58] Field of Search ............................ 606/61, 60, 72, 606/73, 76, 86, 90, 104, 105, 53; 623/17

[56] References Cited

U.S. PATENT DOCUMENTS

| | | |
|---|---|---|
| 4,662,365 | 5/1987 | Gotzen et al. . |
| 4,790,297 | 12/1988 | Luque . |
| 4,913,134 | 4/1990 | Luque . |
| 4,946,458 | 8/1990 | Harms et al. . |
| 4,987,892 | 1/1991 | Krag et al. . |
| 5,002,542 | 3/1991 | Frigg . |
| 5,047,029 | 9/1991 | Aebi et al. . |
| 5,084,049 | 1/1992 | Asher et al. ............................. 606/61 |
| 5,092,893 | 3/1992 | Smith ...................................... 623/17 |
| 5,108,395 | 4/1992 | Laurain . |
| 5,127,912 | 7/1992 | Ray et al. . |
| 5,261,907 | 11/1993 | Vignaud et al. ......................... 606/60 |
| 5,261,909 | 11/1993 | Sutterlin et al. ......................... 606/61 |
| 5,282,801 | 1/1994 | Sherman .................................. 606/61 |
| 5,334,203 | 8/1994 | Wagner .................................... 606/61 |

FOREIGN PATENT DOCUMENTS

| | | |
|---|---|---|
| 3219575 | 5/1982 | Germany . |
| 780652 | 8/1957 | United Kingdom ..................... 606/61 |
| 8200084 | 1/1982 | United Kingdom . |

OTHER PUBLICATIONS

Compte, Pierre "Metallurgical Observations of Biomaterials "*Contempory Biomaterials* Boretos ed. Noyes Publications, Park Ridge New Jersey, 1984, pp. 66–91.
"TSRH Spinal System Design Rationale"; pp. 1–11; Danek Group, Inc., 1992 Memphis, Tennessee, Author unknown.
Excerpts from *TSRH Crosslink$_{198}$*, Surgical Manual; pp. 1–2, 4–8; Danek Medical, Inc., Memphis, Tennessee, Author unknown, Date unknown.
Moss; Excerpts from *Titanium–Mesh–Cylinder*; West Germany, Harms et al Date unknown.
Moss; Excerpts from *Bone screw with adjustable head*; West Germany, Harms et al. Date unknown.
Excerpts from *The TRSH Spinal Implant System*; pp. 1–14, 16, Date & Author unknown.
Excerpts from *Modular Segmental Spinal–Instrumentation*; West Germany, Date & Author unknown.
AcroMed; Excerpts from *ISOLA®Spinal System*; 1991; Cleveland Ohio, USA Author unknown.
"Spinal Stability and Instability: Definitions, Classification, and General Principles of Management", *The Unstable Spine*, by J. Frymoyer, et al., pp. 1–10 1986.

(List continued on next page.)

Primary Examiner—Guy V. Tucker
Attorney, Agent, or Firm—Knobbe, Martens, Olson & Bear

[57] ABSTRACT

An apparatus and method for using a titanium alloy skeletal fixation system. A vertically adjustable spine screw includes an elongated u-shaped yoke on one end, with a machined female slot on each yoke side. The female slots allow ease of gripping the spine screw with a modified forceps like device. Parallel malleable metallic rods are conformed to the spinal region, then connected to the screw using an eyebolt assembly. This eyebolt assembly includes an angular rotation spacer, and a height adjustment spacer with positioning tabs. This assembly slides over each parallel rod with the bolt portion slipping into the spine screw yoke. The yoke meshes with the height adjustment spacer allowing height adjustment. The angular rotation spacer conforms to the rod and the height adjustment spacer. One or more of three different bridge assemblies transversely span the essentially parallel rods allowing lateral and angular adjustment.

6 Claims, 10 Drawing Sheets

OTHER PUBLICATIONS

Excerpts from *Materials Used in Spine Stabilization*, Malinin, et al., pp. 30–32, Date unknown.

"Current Concepts of Internal Fixation", *The Unstable Spine*, by A. Khan, III, pp. 45–83 1986.

"Surgical Stabilization in Cervical Spine Trauma", *The Spinal Cord Injured Patient: Comprehensive Management*, by D.A. Capen, M.D. 1991.

"Anatomic and Technical Considerations of Pedical Screw Fixation", *Clinical Orthopaedics and Related Research*, by J.N. Weinstien, D.O., et al., pp. 34–46 (Nov. 1992).

"The Use of Intrapedicular Fixation Systems in the Treatment of Thoracolumbar and Lumbosacral Fractures"*Orthopedics*, by M. Zindrick, et al. pp. 337–341 (Mar. 1992).

"A Biomechanical Analysis if Zielke, Kaneda, and Cotrel–Dubousset Instrumentations in Thoracolumbar Scoliosis"*SPINE*, by Y. Shono, et al., pp. 1305–1311 (Nov. 1991).

"Experimental Evaluation of Seven Different Spinal Fracture Internal Fixation Devices Using Nonfailure Stability Testing" *SPINE*, by R. W. Gaines, Jr., et al., pp. 902–909 (Aug. 1991).

"Triangulation of Pedicular Instrumentation", *SPINE*, by C. M. Ruland, et al., pp. s270–s276 (Jun. 1991).

"The Role of Transpedicular Fixation Systems for Stabilization of the lumbar Spine", *Orthopedic Clinics of North America*, by M. R. Zindrick, pp. 333–344 (Apr. 1991).

"A pedicle screw bridging device for posterior segmental fixation of the spine: preliminary mechanical testing results"*Journal of Biomedical Engineering*, by A. T. Rahmatalla, et al., pp. 97–102 (Mar. 1991).

"Long–Term Lumbar Facet Joint Changes in Spinal Fracture Patients Treated with Harrington Rods", *SPINE*, by V. O. Gardner, et al., pp. 479–484 Jun. 1990.

"Anterior Kostuik–Harrington Distraction Systems for the Treatmant of Kyphotic Deformities", *SPINE*, by J. P. Kostuik, pp. 169–180 Mar. 1990.

"Biomechanical Analysis of Pedicle Screw Instrumentation Systems in a Corpectomy Model", *SPINE*, by R. Ashman, et al., pp. 1398–1405 Dec. 1989.

"Biomechanical Analysis of Posterior Instrumentation Systems After Decompressive Laminectomy", *Journal of Bone and Joint Surgery*, K. R. Gurr pp. 680–91 Jun. 1988.

"The Role of Harrington Instrumentation and Posterior Spine Fusion in the Management of Adloescent Idiopathic Scoliosis", *Orthopedic Clinics of North America* by T. S. Renshaw, pp. 257–267 (Apr. 1988).

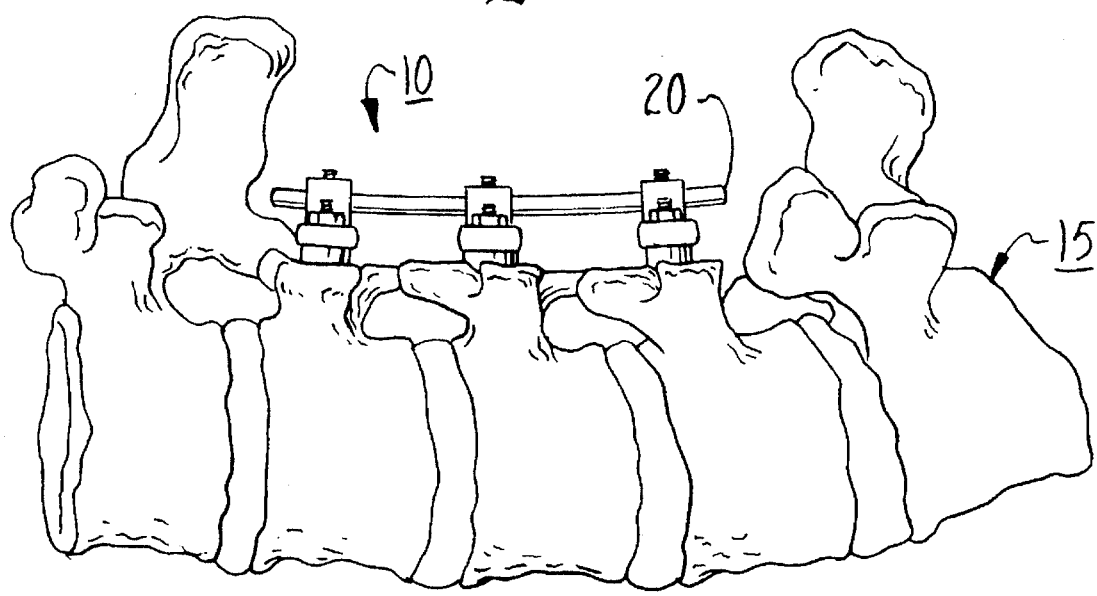
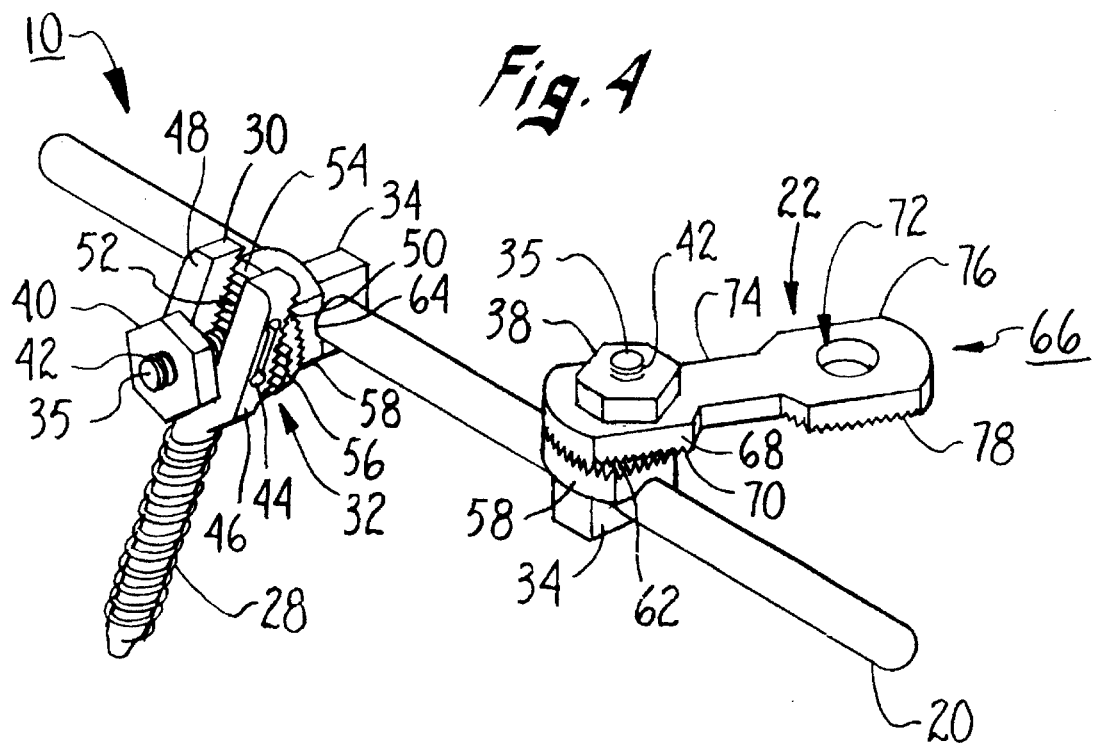

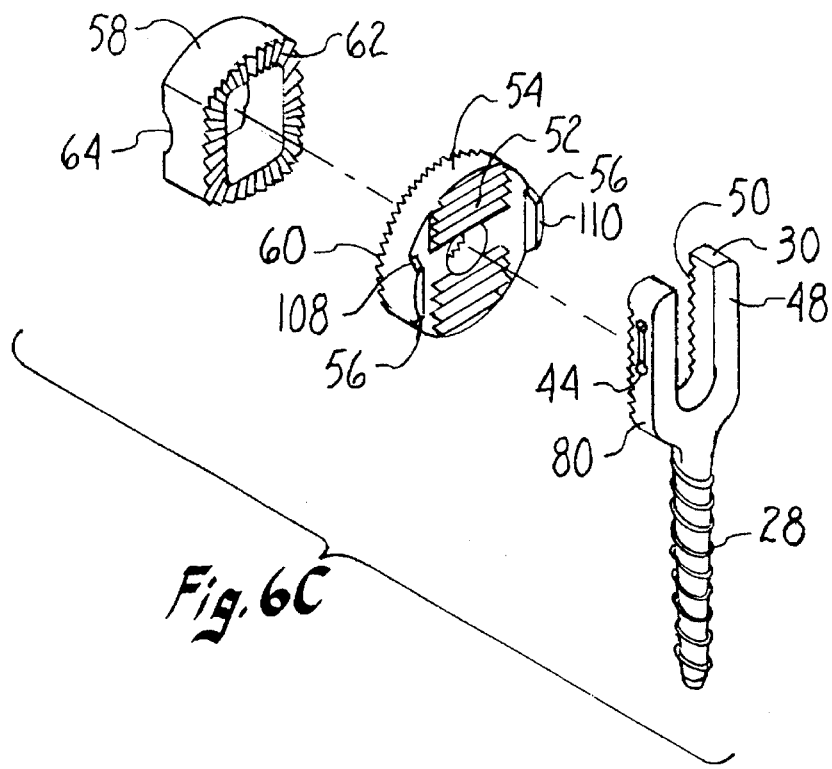
Fig. 6C
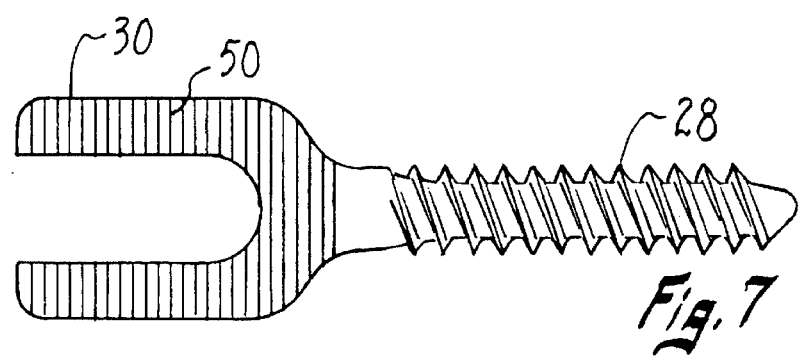
Fig. 7
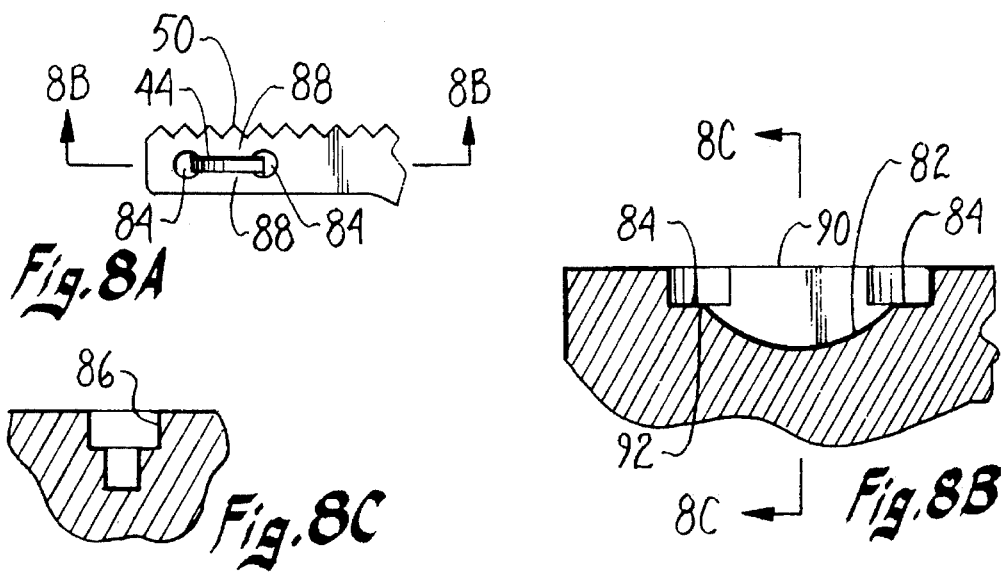
Fig. 8A
Fig. 8B
Fig. 8C

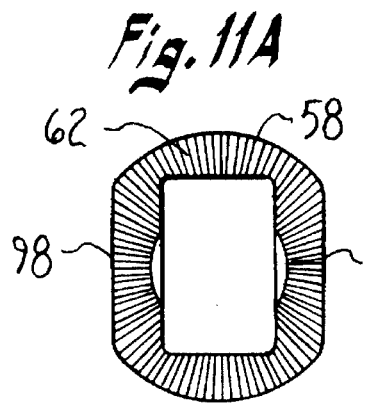 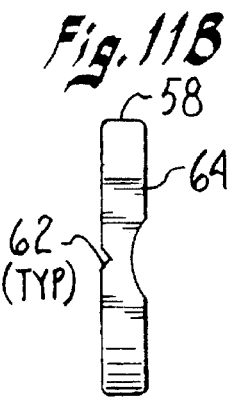 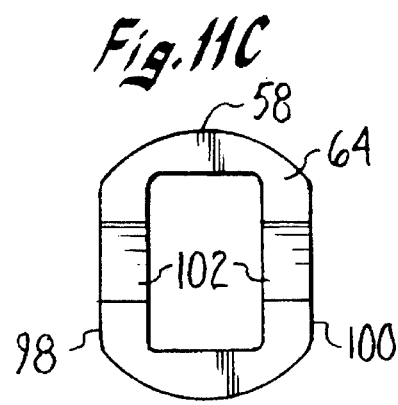
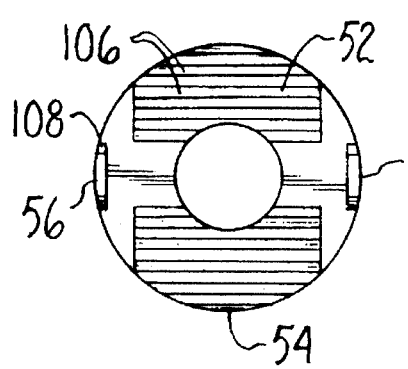 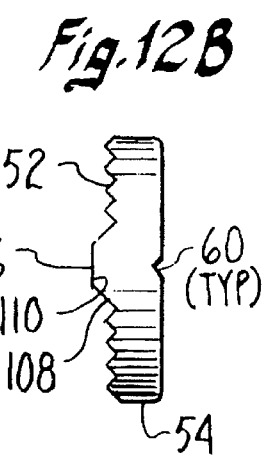 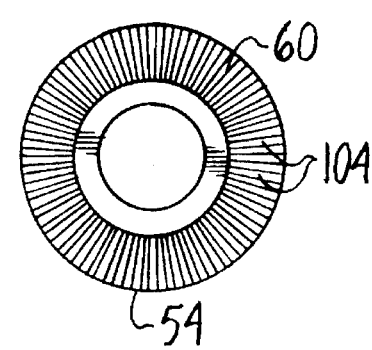
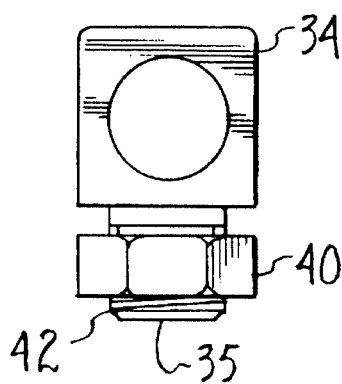

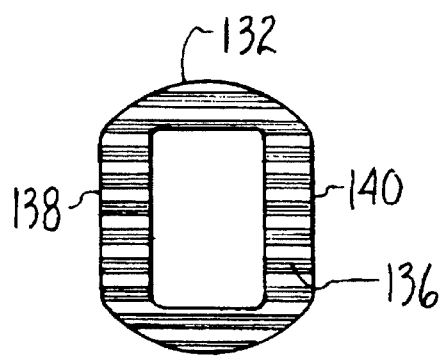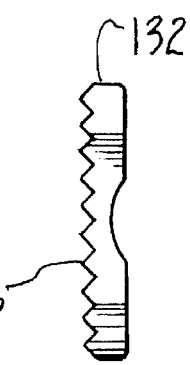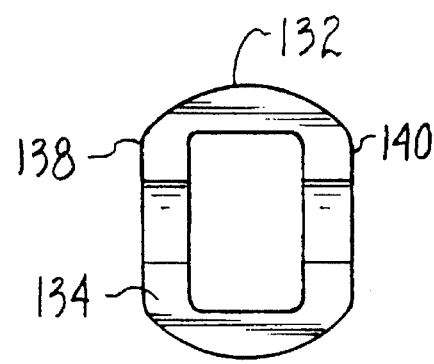
Fig. 18A    Fig. 18B    Fig. 18C
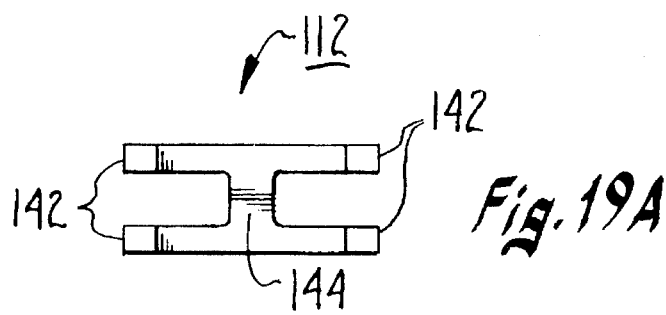
Fig. 19A
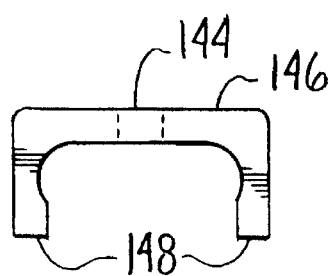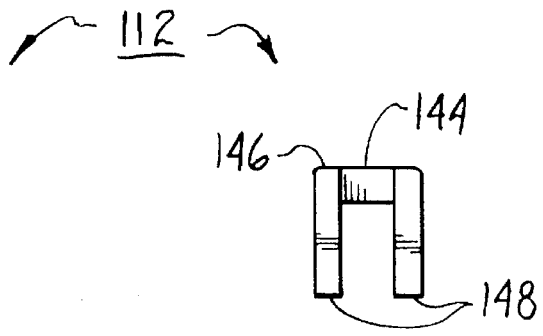
Fig. 19B    Fig. 19C

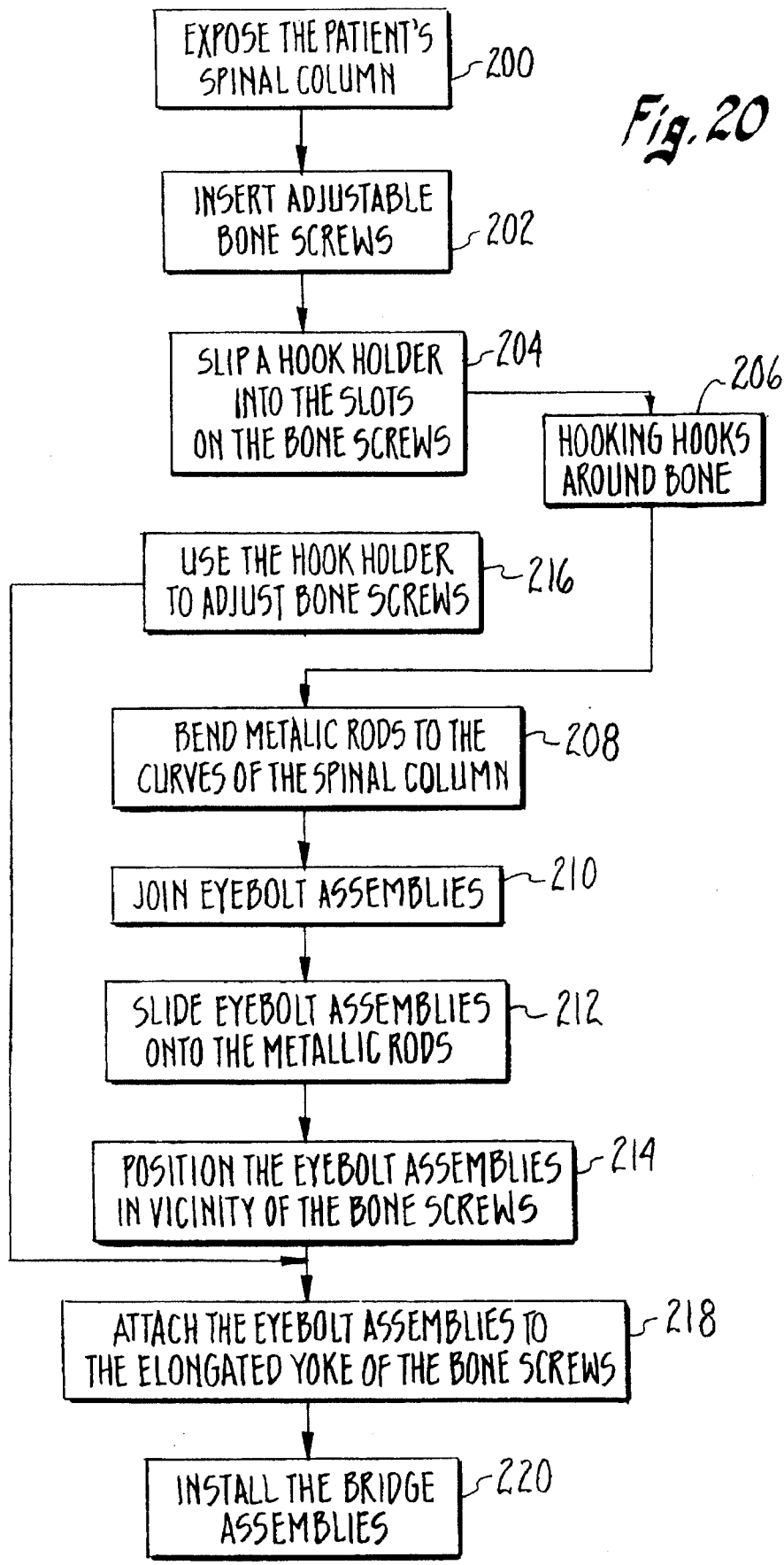

APPARATUS FOR SPINAL FIXATION SYSTEM

This application is a continuation of application Ser. No. 08/020,288, filed Feb. 19, 1993, now abandoned.

FIELD OF TECHNOLOGY

This invention relates to prosthetic devices used in skeletal fixation systems, such as those used with degenerative, trauma, and deformity conditions.

BACKGROUND

A wide variety of spinal fixation systems exist. Some systems and their components will be discussed below, and are well known to those skilled in the art of orthopedic. These various systems are meant to provide a safe technique, a secure and stable implant of the components or constructs, and provide sufficient force to the spine to correct deformities, or aid in an healing process from trauma, or assist in degenerative conditions. In addition, these implants or constructs must resist fatigue and failure post operatively until bone fusion occurs.

The forces applied to the functional spinal unit include compression, tension, torsion, and shear. The motion associated with a spine is complex. Rotations and translations occur about three axes and result in six possible components of movement for any motion. It is therefore important that a spinal fixation unit for surgical implantation provide a high degree of stability.

An orthopedic surgeon typically employs the following protocol for installation of a spinal fixation device. The patient is positioned on an appropriate frame, such as an Andrew's frame or operating table, and is prepped and draped in the fashion standard for back surgery. The incision is made over the spinous process of the area to be decompressed. The incision is carried down through the dorsal lumbar fascia and the fascia is then incised down to the spinal lamina junction. Dissection is continued out to the tips of the transverse processes and is accomplished using the electrocautery and Cobb dissection tool. Self retaining retractors are then placed into the wound to allow clear visualization of the structures which have been denuded of their soft tissue. Further meticulous soft tissue dissection is performed with the removal of the supraspinous ligament and the interspinous ligament for the vertebral levels to be addressed in the surgery process. Intraoperative lateral x-ray confirms the position at the appropriate level, such as the thoracic, lumbar, or sacral levels. After implanting the spinal fixation device, the wound is then closed using standard operating procedures.

Use of pedicle screws is typical with instrumentation systems such as a Dynamic Transverse Traction (DTT) unit, the Steffee-VSP system (AcroMed Corporation), Isola Instrumentation (AcroMed Corporation, Cleveland, Ohio), or the like. Harrington devised the first universally accepted method of internal fixation for the treatment of spinal deformity. The current Harrington method uses stainless steel constructs. In 1974 Zielke developed a bone screw with a slotted head. In 1982 he used it for the first time through the pedicle of the vertebral arch, to correct kyphotic posture defects. These instrumentation devices are useful where lumbar segmental instability is a problem. Zielke's method, termed the VDS system, uses stainless steel.

Another system is the TSRH (Texas Scottish Rites Hospital) Spinal System, by Danek Medical, Inc. This system provides temporary stabilization until a solid spinal fusion develops. Use is indicated for such conditions as idiopathic scoliosis, neuromuscular scoliosis with associated paralysis or spasticity, spinal fractures, and neoplastic disease. Deficient posterior elements resulting from laminectomy or spina bifida could call for use of bone screws. Still another system uses the Galveston technique for pelvic fixation. A different approach to using bone screws is that of the MOSS-Titanium-mesh-cylinder system for spinal tumors between cervical vertebrae C3 and lumbar vertebrae L5. The MOSS-bonescrew-system is used for postural defects between thoracic vertebrae Th8 and sacrum S1. Other systems, such as the Dwyer system, use wire or cable as a securing device for the constructs. Wire tends to provide less stability for certain conditions. Different conditions require creating forces artificially to correct or maintain the spinal orientation. Posterior compression, anterior bone block, reposition by distraction, or anterior release are just some of the force applications for different conditions.

Pedicle screws, hooks, eyebolt assemblies, hex nuts, transverse rods, and cross-links are associated with these devices. Current pedicle screws have a yoke that has a u-shaped grove that conforms directly to a transverse rod. Both surfaces of the yoke are flush. The hex nut holds against the small yoke. However, hex nuts tend to loosen under the thousands of daily stresses experienced by the spine, unless they are securely fastened. This construct requires bending of the rod in order to conform to the lordotic (concave) or kyphotic (convex) curves in the surgical area. It is important to avoid excessive bending and rebending of these rods because fatigue resistance decreases as bending increases, leading to a more likely rod failure. Eyebolts can also score these rods, leading to earlier rod failure. On the other hand, some rods are too stiff, such as stainless steel rods, and do not lend themselves to contouring, although contouring is a positive characteristic in a rod.

Some existing washer-like spacers used between the rod and the bone screw provide for angular rotation of a pedicle or bone screw. However, they do not provide for height adjustment of the eyebolt assembly. Existing cross links have grooves in the center of rectangular ends on each cross link. This feature means that the essentially parallel rods must be exactly parallel or the cross link does not fit. Therefore other constructs are needed to stabilize the vertebral body area.

In certain areas of the spine, high stresses are created in the rods. Some systems avoid cross links in these areas because the stress would be too great and prevent stability from being achieved or being maintained. The links would fail. Contraindications occur with many devices for certain situations because of lack of their versatility for use in multiple circumstances.

Problems that exist in current spinal fixation systems include 1) lack of adequate strength in metallic rods, 2) lack of flexibility in the use of metallic rods, 3) severe stresses occurring within the constructs, 4) lack of height adjustment of the constructs, 5) lack of angular rotation capability within the bridge assemblies, 6) difficulty in locating and holding the bone screw with a forceps like device, and 7) difficulty in securing the eyebolt assembly into the yoke of the bone screw.

Thus, there is a continuing need for apparatus and methods for improving skeletal fixation systems, particularly in stabilizing spinal vertebrae under degenerative, trauma, or deformity conditions.

SUMMARY OF THE INVENTION

The above problems, and others, are overcome by the apparatus and method of this invention in which a skeletal fixation system is used for providing stability to bones, such as those found in the spinal column, after degeneration, trauma, or when deformity exists. Additionally, application of the present invention may be found in the larger human bones of the arm or leg, specifically, bones such as the humerus, ulna, radius, or tibia. Basically, this novel system uses various combinations and variations, in desired arrangements and configurations, of the various components of the invention. Each of these configurations is called a construct. The constructs of the present invention will be described in the context of their use.

The constructs for this fixation system are numerous. The components of each construct are a bone screw, a hook, a rod, an eyebolt assembly, and a bridge assembly. The eyebolt assembly includes an eyebolt, an angular rotation spacer, a height adjustment spacer, and a hex nut. The bridge assembly includes several embodiments of bridges, an angular rotation spacer, an eyebolt and a hex nut. All components are made of a metallic composition, and all are surface treated with a chemical dipping process.

One possible, and preferred construct, has eyebolt assemblies connected to one or more bone screws. Then the rods fit through the eyebolts. One of three bridge assembly embodiments, preferably a bridge plate, is connected to the generally parallel rod pair. The eyebolt assembly for the bone screw would use both the angular rotation spacer and the height adjustment spacer. The bridge assemblies would use an angular rotation spacer, and a lateral adjustment spacer.

The bone screw, which is height or generally vertically adjustable, has several novel features. One end is an elongated u-shaped yoke. One surface of this end is serrated with straight or parallel, or teeth-like grooves. These grooves are oriented across the surface of the yoke, not vertically along the sides of the yoke. The other surface of the yoke is flat or flush.

Another novel feature is two machined female slots, one on each side of the yoke. These female slots fit into two male probes on, a modified forceps-like device. These internally affixed male probes are generally located on each end of the inner surface of the opposing gripping arms of the modified forceps. The female slots are of a funneling design, both vertically and horizontally, for ease of aligning with the male probes, when used.

The rod is typically and preferably used in essentially parallel pairs. The rods are generally flexible and malleable to allow bending to match the curves of the vertebral body. And these rods are oriented generally parallel to the spinal column.

The eyebolt assembly generally has the angular rotation spacer next to the eyebolt, then the height adjustment spacer is on top of the first spacer, followed by the bone screw and the hex nut. For the bridge assembly, the angular rotation spacer is next to the eyebolt. Then a bridge embodiment is on top of this spacer, followed by a hex nut, which is larger than the hex nut used with the bone screw. Three embodiments of the bridge are a bridge plate, a modular bridge, and a low profile bridge.

The method of use or installation of this skeletal fixation system involves how the above-mentioned components are assembled and how they work together in various constructs.

Advantages of the present invention include 1) adequate strength in all component parts by using a titanium alloy, 2) flexibility and fatigue strength in the use of metallic components by using titanium alloy, 3) reducing stresses occurring within the constructs by building in a more forgiving construct which reduces the need to force the vertebra to fit the construct and being more stable, 4) providing a height adjustment capability of the constructs by using a specially designed spacer, 5) including angular rotation and width variability within the bridge assemblies, 6) ease of locating and holding the bone screw and hooks by machining into the bone screw yoke and hook body a set of slots, and matching these slots with a modified forceps like tool, 7) ease in securing the eyebolt assembly into the yoke of the bone screw by using a partially preassembled eyebolt assembly by staking the end of the bolt portion of the eyebolt assembly, 8) reducing surgery time and induced trauma because less time is required to adjust the constructs in the present invention, and 9) since the parts are made from non magnetic titanium, magnetic resonance (MR) can be used to observe the spinal cord and other soft tissue that cannot be observed with traditional x-ray. This cannot be done with stainless steel, because the reflection obscures any diagnostic viewing.

These and other aspects of the apparatus and method of the skeletal fixation system of the present invention are set forth more completely in the accompanying figures and the following description.

BRIEF DESCRIPTION OF THE DRAWINGS

Details of the invention, and of the preferred embodiments thereof, will be further understood upon reference to the drawings, wherein:

FIG. 3 is a lateral view of the construct of the present invention in place on the spinal column.

FIG. 4 is a perspective view of a preferred construct of the present invention.

FIG. 6c is a exploded schematic view of the adjustable spine bone screw device showing the assembly relationship of the spacers and bone screw in the present invention.

FIG. 7 is a front elevation view of one embodiment of the bone screw of the present invention.

FIG. 8a is a schematic partial vertical section cutaway view of the female slot in each side of the bone screw device.

FIG. 8b is a plan view of the female slot shown in FIG. 8a.

FIG. 8c is a partial cross section cutaway view of the female slot shown in FIG. 8a.

FIG. 10b is an elevation view of the male probe shown in FIG. 10a.

FIG. 11a is a plan view of an embodiment of the angular rotation spacer.

FIG. 11b is an elevation view of the angular rotation spacer shown in FIG. 11a.

FIG. 11c is a plan view of the underside of the angular rotation spacer shown in FIG. 11a.

FIG. 12a is a schematic view of an embodiment of the height adjustment spacer with radially extending serrations on one side that allow angular rotation and transverse or parallel serrations with positioning tabs on the other side that allow height adjustment. This spacer is available in varying widths to allow width adjustment. Also illustrated are the positioning tabs.

FIG. 12b is an elevation view of the height adjustment spacer shown in FIG. 12a.

FIG. 12c is a plan view of the underside of the height adjustment spacer shown in FIG. 12a. The radially extended serrations in this view allow meshing with the angular rotation spacer shown in FIG. 11a.

FIG. 13 is a schematic view of a typical eyebolt device used with the present invention.

FIG. 14 is a schematic view of an embodiment of a typical section of a metallic rod used with the present invention.

FIG. 18a is a plan view of a variation on the height adjustment spacer used with the bone screw. This variation is also used as a lateral adjustment spacer with the modular bridge embodiment of the bridge assembly.

FIG. 18b is a front view of a variation on the straight serrated spacer. This variation is used with the modular bridge embodiment of the bridge assembly.

FIG. 18c is an underside view of a length variation on the straight serrated spacer. This view shows the flush surface of the spacer that conforms to one of the essentially parallel rods.

FIG. 19a is a plan view of an alternate embodiment of a low profile bridge.

FIG. 19b is a front view of a variation on the low profile bridge third embodiment of the bridge assembly.

FIG. 19c is a side elevation view of a variation on the low profile bridge third embodiment of the bridge assembly.

FIG. 20 is a block diagram illustrating the method of installing the spinal fixation system shown in FIG. 1.

DETAILED DESCRIPTION OF THE PREFERRED EMBODIMENTS

Figure 1:
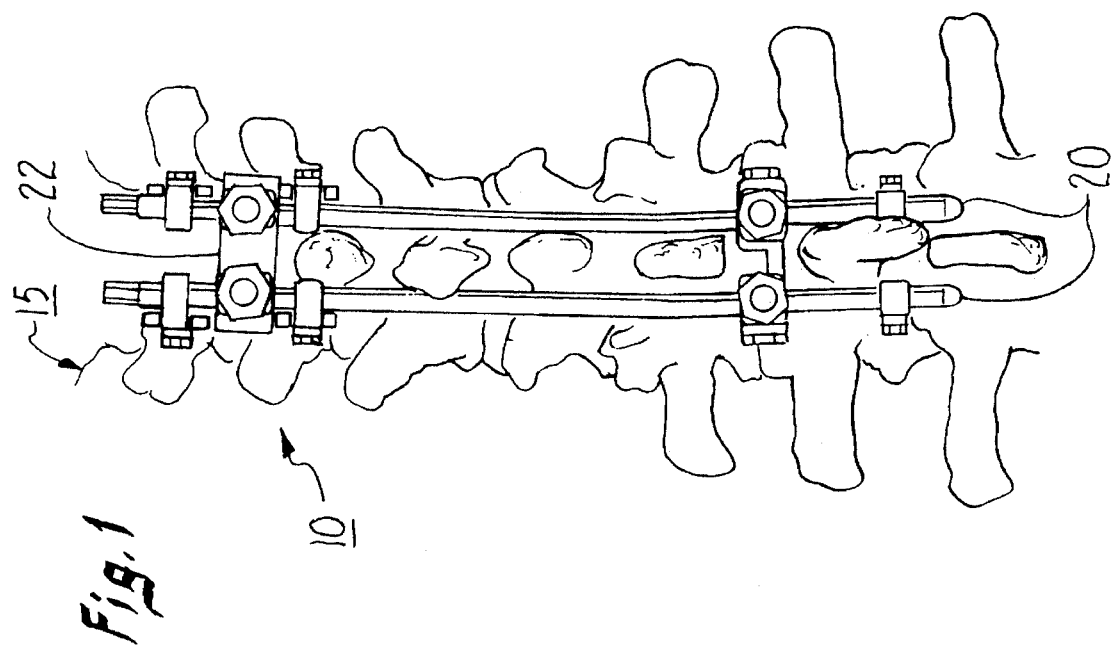
FIG. 1 is a plan view of a preferred embodiment of the spinal fixation system apparatus in place on a skeletal spinal column.

Referring initially to FIG. 1, there is seen a perspective plan view of an embodiment of the spinal fixation system apparatus 10 in place on an isolated skeletal spinal column 15. This spinal column 15 is shown in stabilized position.

Figure 2:
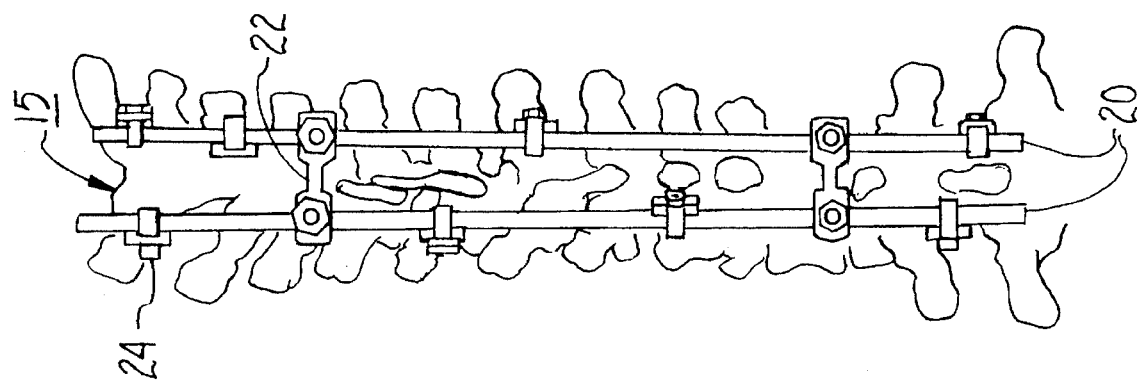
FIG. 2 is a plan view of a different embodiment of the spinal fixation system in place on a skeletal spinal column.

Referring now to FIG. 2, there is seen a second perspective plan view of the spinal fixation system showing a different embodiment. This isolated spinal column is shown stabilized in a deformity condition.

Referring next to FIG. 3, there is seen a detail perspective front view of an embodiment of the present invention, as installed in a spinal column.

Referring to FIG. 4, there is seen a detail perspective angled view of a preferred embodiment of the present invention, showing more detail of bone screw 28 and bridge assembly 22.

Figure 5A:
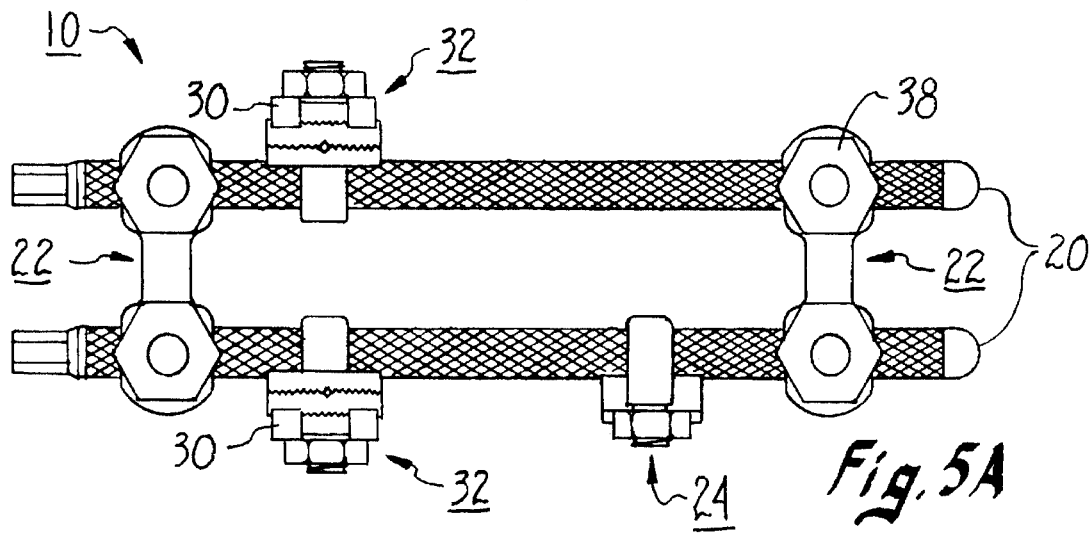
FIG. 5a is a top view of a construct of the present invention.

Referring now to FIG. 5a, there is seen a detail schematic top view of the present invention. Bridge assembly 22 interconnects horizontally or transversely with and is removable from rod 20. The bridge assembly 22 can allow lateral or width adjustments, or angular movement, depending on the embodiment.

The rods 20 typically and preferably are two essentially straight and parallel rods. FIG. 5a. These rods 20 are made of a flexible and bendable material. This material is a metallic composition, preferably a titanium alloy. Further, preferably this titanium alloy is Ti6A14V. This alloy is chosen for being bendable in rod form, yet strong enough to withstand the many and possibly severe stresses within a spinal fixation system 10 (FIG. 1). The forces involved in installing and using the components as well as after surgery, are many. It is appropriate to use such an alloy to reduce metal fatigue to help prevent breakage during installation or during the post-operative and recovery phase.

Seen in this view is a general construct using two essentially parallel rods 20 transversely spanned by a bridge assembly 22.

A typical hook 24 used in many fixation systems is hooked around the lamina portion of the spinal column 15 (FIG. 3).

Also seen is one of the pair of essentially parallel rods 20. This view shows rod 20 as curved, conforming to spinal column 15 (FIG. 3). The U-shaped elongated yoke 30 of bone screw 28 is shown in one of several possible orientations. The bridge assembly 22 shows eyebolt assembly 32 with an eyebolt, bridge assembly 22, and bridge assembly restraining hex nut 38 in an assembled view.

Referring now to FIG. 4. In this view, eyebolt restraining hex nut 40 is shown screwed onto bolt portion 42.

This eyebolt nut 40 requires sufficient torque to hold firmly in place the bone screw 28 and the eyebolt assembly 32. Also seen is one of the two female machined slots 44, located on a first side 46 of elongated yoke 30. The slots 44 are centrally located generally at the top of yoke 30.

Yoke 30 has a flush outer surface 48 that tangentially touches eyebolt hex nut 40. The parallel serrated inner surface 50 of yoke 30 is shown meshing with the parallel serrated outer surface 52 of height adjustment spacer 54.

One of two positioning tabs 56 is seen in this view. These positioning tabs 56 provide a guide to yoke 30, so that the yoke 30 properly meshes with height adjustment spacer 54.

Meshing with height adjustment spacer 54 is angular rotation spacer or adapter 58. Radially extended serrated inner surface 60 (FIG. 6c) of height adjustment spacer 54 is shown meshing with the radially extended outer surface 62 (FIG. 6c) of angular rotation spacer or adapter 58. The flush grooved inner surface 64 of angular rotation spacer or adapter 58 is shown tangentially touching rod 20. This grooved inner surface 64 matches the diameter of rod 20.

The bridge assembly 22 shown includes eyebolt 34, angular rotation spacer or adapter 58, a preferred embodiment of bridge plate 66, and bridge assembly hex nut 38. Angular rotation spacer 58 matches rod 20 as previously described. A first end 68 of bridge plate 66 has a radially extended serrated lower surface 70 that meshes with radially extended serrated outer surface 62 of angular rotation spacer or adapter 58. Flattened top 72 of bridge plate 66 tangentially touches bridge assembly hex nut 38.

The first end 68 is integrally joined with connecting piece 74, and this connecting piece 74 is integrally joined with second end 76. Second end 76 has an identically machined radially extended serrated lower surface 78 as does first end 68. Surface 78 would mesh with another angular rotation spacer 58 as part of a bridge assembly 22 (FIG. 5a) on another rod 20.

All components in the various constructs are preferably Ti6A14V. And all components are overall surface treated to prevent galling and fretting. Galling could be considered scuffing or denting of metal due to friction between metallic parts. Fretting could be considered a breaking away of metallic pieces due to friction between parts. This surface treatment is done in an interstitial process. This process is a chemical process where each part is dipped into a chemical bath.

Referring now to FIG. 5a, also seen is eyebolt assembly 32, with is components previously identified. A typical hook 24 is also shown as a component in a typical construct.

Figure 5B:
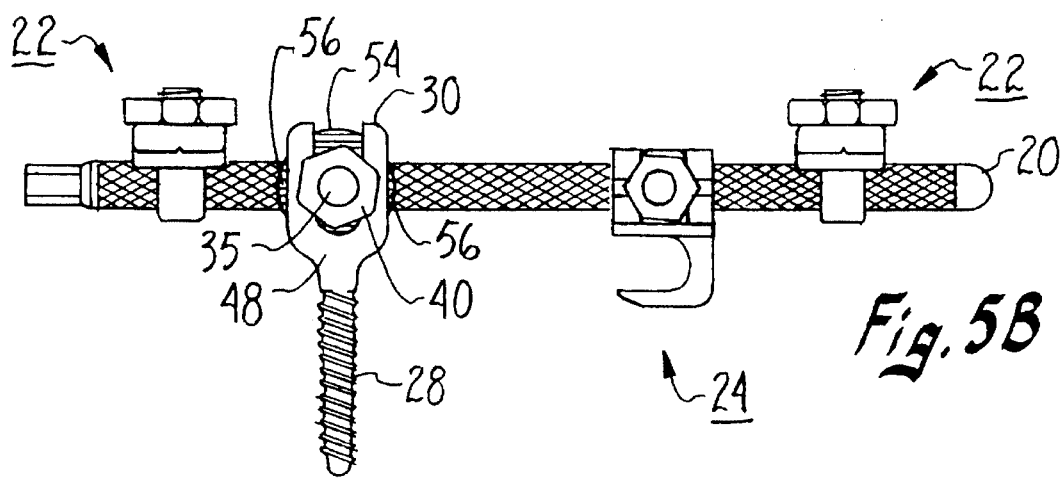
FIG. 5b is a lateral view of a construct of the present invention.

Referring to FIG. 5b, there is seen a detail schematic front view of the present invention. An eyebolt assembly is shown. The bone screw 28 is also shown.

More clearly shown in this view is the bone screw 28, first shown in FIG. 3. Also more clearly shown is the parallel serrated outer surface 52 of height adjustment spacer 54. This bone screw 28 is inserted by a surgeon into the pedicle area of the spinal column 15 (FIG. 3), on either a human or animal, through a pretapped hole with a bone screw inserter. Special designed hooks 24 which are positioned between the vertebra are also used in stabilizing the spinal column 15 (FIG. 3). Final positioning of the screws 28 and hooks 24 is facilitated by using a modified forceps device 94 (see FIG. 9). These forceps 94 have male probes integrally affixed to the opposing gripping arms 98 of the forceps 94.

Figure 6A:
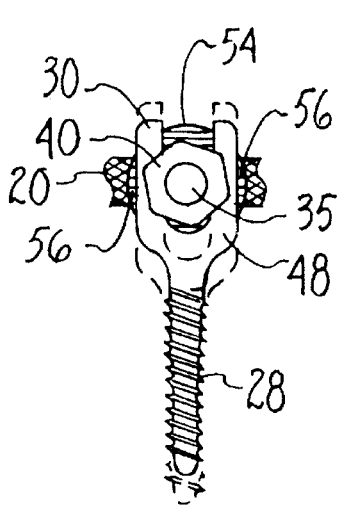
FIG. 6a is an elevation view of an adjustable spine bone screw device showing the height adjustment feature of the present invention.

Referring next to FIG. 6a, there is seen a detail schematic elevation view of bone screw 28 showing the height adjustment feature. One possible variation is height adjustment of yoke 30 is Shown. In phantom are shown two other variations in height adjustment. Eyebolt restraint nut 56 in the eyebolt assembly is tightened in one of these positions or others, depending on the location of the construct within the pedicle region of the vertebral body of a patient.

Figure 6B:
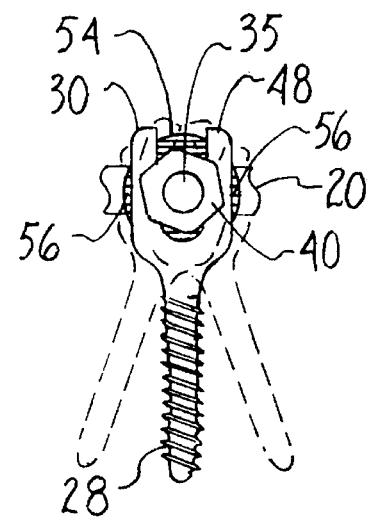
FIG. 6b is an elevation view of the adjustable spine bone screw device showing the rotational adjustment feature of the present invention.

Referring now to FIG. 6b, there is seen a detail schematic elevation view of the bone screw 28 showing the angular rotation adjustment feature. This bone screw 28 is interchangeable with a variety of standard lengths with associated threads per inch. Shown more clearly in this view are some typical angular orientations of bone screw 28. Also shown more clearly than in FIG. 4 are the position tabs 56. These tabs 56 are integrally affixed to height adjustment spacers 54. The tabs 56 are located at the ends of the diameter of height adjustment spacer 54, such that yoke 30 can easily and tangentially fit between the tabs 56. The tabs 56 prevent angular rotation of the spacer 54 with respect to the bone screw 28.

Referring to FIG. 6c, there is seen a detail exploded schematic view of the bone screw 28 showing the assembly relationship of the angular rotation spacer or adapter 58 and height adjustment spacer 54 and bone screw 28. The parallel serrated inner surface 50 on the bone screw 28 is shown. Also shown for the first time is the entire parallel serrated outer surface 52 on height adjustment spacer 54, and showing positioning tabs 56. The entire angular rotation spacer 58 is shown for the first time with the radially extended serrated outer surface 62. Also shown is a view of female slots 44.

Referring to FIG. 7, there is seen a detail schematic view of an embodiment of the bone screw 28. The bone screw 28 is overall surface treated with an interstitial process to prevent galling and fretting.

Referring to FIG. 8a, there is seen a detail schematic of the female slot 44 in first side 46 (FIG. 6c) and second side 80 (FIG. 6c) of yoke 30. These slots 44 are of a funneling design both vertically and horizontally which allows easy alignment with the similarly shaped male probe 96 FIG. 9) of the forceps 94 (FIG. 9).

These identical slots have a rounded bottom 82 (FIG. 8b), and two rounded shrunken shoulders 84. The two slot side surfaces 86 (FIG. 8c) have identically shaped protruding lips 88 extending downward from the slot top 90 (FIG. 8b).

Figure 9:
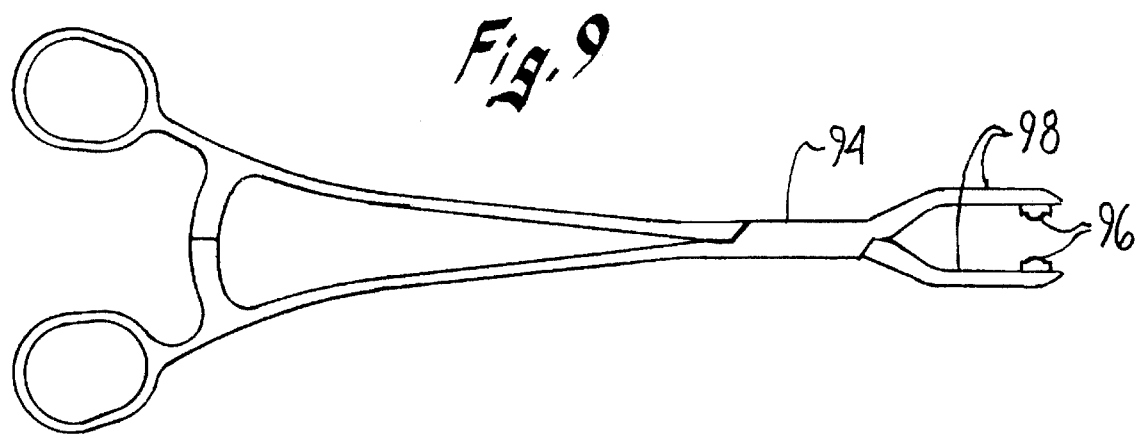
FIG. 9 is a plan view of the modified forceps like device used with the female slots in the bone screw device.

Each slot is of appropriate dimensions to fit over male probe 96 (FIG. 9). Particularly suitable values are about 0.75 inches in depth, about 0.234 inches in length, and about 0.043 inches in width. The lips 88 are about 0.187 in length and about 0.01 inches in width. Slots may be larger or smaller, however, they would have the same proportional geometry.

Referring next to FIG. 8b, there is seen a partial vertical section cutaway view of a female slot. The rounded bottom 82 of the slot has a radius of about 0.125 inches. Other particularly suitable values follow. The sunken shoulders 84 are recessed or sunk about 0.033 inches and protruding horizontally into the female slot until intersected by the upper edge 92 of the rounded bottom 82, about 0.0235 inches.

Referring to FIG. 8c, there is seen a partial cross section cutaway view of the female slot.

Referring to FIG. 9, there is seen a perspective plan view of the modified forceps like device 94 used with the female slots 44 in the yoke 30 (FIG. 6c) of bone screw 28 (FIG. 6c). These modified forceps 94 are generally designated a hook holder. Two opposing male probes 96 are affixed to the gripping arms 98 on the operative end of these forceps 94. These male probes 96 are formed to match the slots 44 (FIG. 6c) in bone screw 28 (FIG. 6c). The primary use of the forceps 94 are to position the hook 24 (FIG. 5b) for proper alignment in eyebolt assembly 32 (FIG. 5a). Another use of these forceps 94 is to grasp bone screw 28 (FIG. 6c) for adjusting as needed.

Figure 10A:
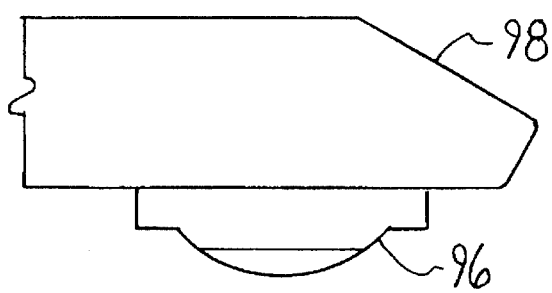
FIG. 10a is a schematic view of the male probe.

Referring to FIG. 10a, there is seen a top view of male probe 96 of appropriate dimensions and adapted to fit female slot 44 (FIG. 6c).

Figure 10C:
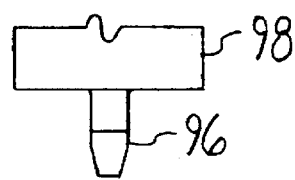
FIG. 10c is a side view of the male probe shown in FIG. 10c.
Figure 10B:
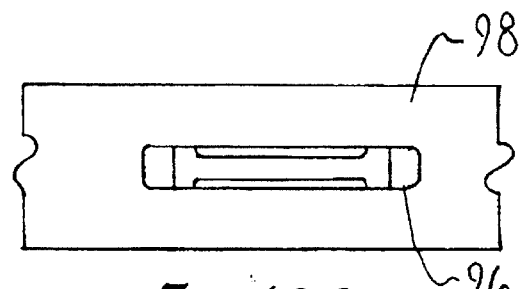

Referring to FIG. 10b, there is seen an elevation view of male probe 96 of approximate dimensions and adapted to fit female slot 44 (FIG. 6c).

Referring now to FIG. 10c, there is seen a side view of male probe 96 of appropriate dimensions and adapted to fit a female slot 44 (FIG. 6c).

Referring now to FIG. 11a, there is seen a detail schematic view of an embodiment of the angular rotation spacer 58 conforming to rod 20 (FIG. 14). This angular spacer or adapter 58 is used with height adjustment spacer 54 (FIG. 12a) and bone screw 28 (FIG. 6c). The radially extended serrated outer surface provides the means for the angular rotation adjustment.

This angular spacer or adapter 58 is generally circular in shape, being reckangularly holed in the center of angular rotation spacer or adapter 58, and further having a horizontal or flattened top 98 and flattened bottom 100. It also has a flattened or thin thickness, of approximately 0.115 inches. The inner surface 64 is machined to conform to the rounded shape of the rod 20 (FIG. 14). The inner surface 64 (FIG. 11c) has a concave shaped groove 102 (FIG. 11c) of identical diameter as rod 20 (FIG. 14). This groove 102 is centered in the inner surface 64, and extends across the entire length of the inner surface 64.

Referring to FIG. 11b, there is seen an elevation view of an angular rotation spacer or adapter 58. The flush grooved inner surface 64 also shown.

Referring to FIG. 11c, there is seen the flush grooved inner surface 64 is shown in its entirety.

Referring to FIG. 12a, there is seen a detail schematic view of an embodiment of the height adjustment spacer 54 used with the angular rotation spacer or adapter 58 (FIG. 11a) and the bone screw 28 (FIG. 6c). Also illustrated are the positioning tabs 56 on the height adjustment spacer 54. This height adjustment serrated spacer provides means for an elevation or height adjustment of the eyebolt assembly 32 (FIG. 5a).

This spacer 54 is also generally circular in shape, being circularly holed in the center of this spacer 54. This spacer 54 also has an inner surface 60 (FIG. 12c) which has radially extending serrations 104 (FIG. 12c), and an outer surface which has parallel serrations 106. The flattened thickness is approximately 0.125 inches.

Referring now to FIG. 12b, there is seen an elevation view of height adjustment spacer 54. One of the positioning tabs 56 is more clearly shown. This height adjustment spacer 54 also has positioning tabs 56 on the outer surface 52. These tabs 56 are opposite each other and are integral part of the height spacer 54. These tabs 56 are approximately 0.030 inches in height and about 0.025 inches in depth. These tabs 56 are beveled on both edges 108 and the top 110.

Referring to FIG. 12c, there is seen the radially extended serrated inner surface 60 in more detail.

Referring next to FIG. 13, there is seen a schematic view of eyebolt 34 used with the present invention or other spinal fixation systems. This eyebolt 34 slides on one or more of the rods 20 (FIG. 14), and then connects to bone screw 28 (FIG. 6c). Also shown is eyebolt restrained hex nut 40.

The eyebolt 34 comes in various sizes. The associated restraint hex nut 40 is of various diameters from about 0.375 to 0.500 inches.

The overall surface is treated with an interstitial process to prevent galling and fretting.

Referring now to FIG. 14, there is seen a schematic view of an embodiment of a section of metallic rod 20. The rod 20 preferably is used in pairs. Due to varying vertebral width and deformity, the rods have some angulation off parallel. The rod 20 is connected to the eyebolt assembly 32 (FIG. 5a), and is of flexible and malleable composition. The rod 20 is essentially straight and paired in variable lengths as required, along the spinal column 15 (FIG. 3). This rod 20 is also of variable diameters, as required, from about 0.250 to 0.281 inches. These rods may be bent to conform to the spine.

This rod 20 is overall surface treated with an interstitial process to prevent galling and fretting. The process is a chemical dipping process. One such preferred surface treating process for use with all of the treated parts of the present invention is known as the TIODIZE process, of the Tiodize Company, Huntington Beach, Calif.

Figure 15A:
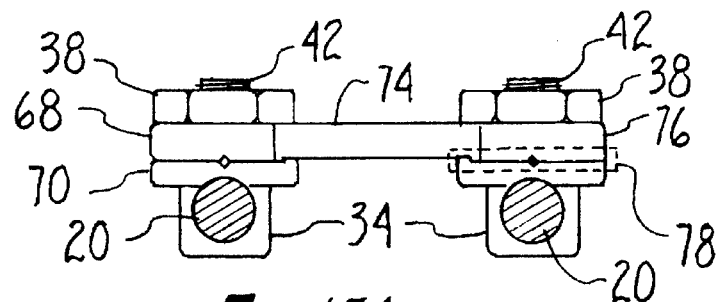
FIG. 15a is a partial front section view of a preferred embodiment of a bridge assembly, specifically the bridge plate embodiment.

Referring to FIG. 15a, there is seen a partial section schematic front view of a preferred embodiment of a bridge assembly, specifically the bridge plate 66 embodiment.

Figure 15B:
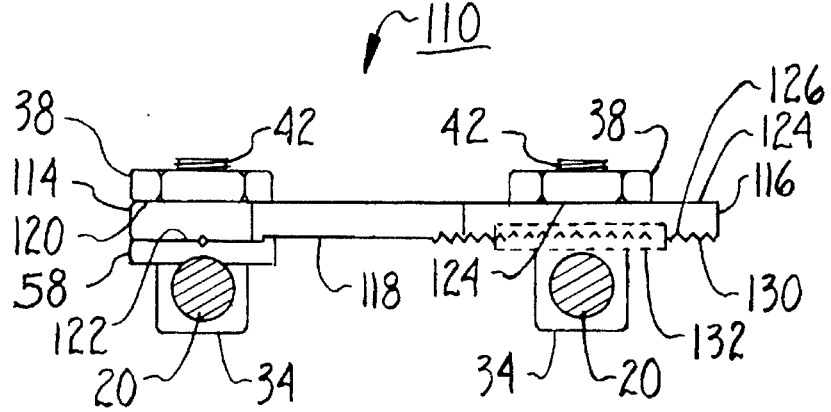
FIG. 15b is a partial front section view of a second embodiment of a bridge assembly, specifically the modular bridge embodiment.

Referring next to FIG. 15b, there is seen a partial section schematic front view of a second embodiment of a bridge assembly, specifically the modular bridge 110 embodiment.

Figure 15C:
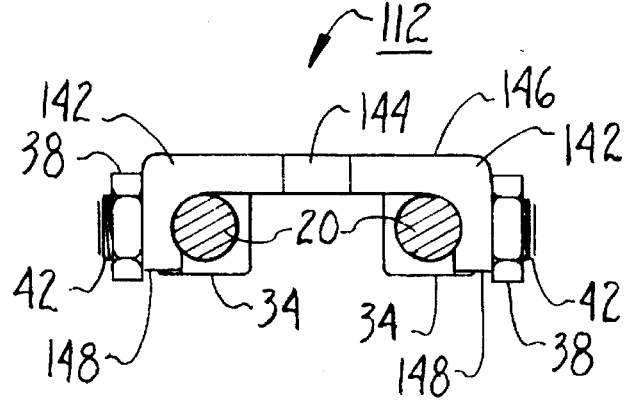
FIG. 15c is a partial front section view of a third embodiment of a bridge assembly, specifically the low profile bridge embodiment.

Referring now to FIG. 15c, there is seen a partial section schematic front view of a third embodiment of a bridge assembly, specifically the low profile bridge 112 embodiment.

Figure 16A:
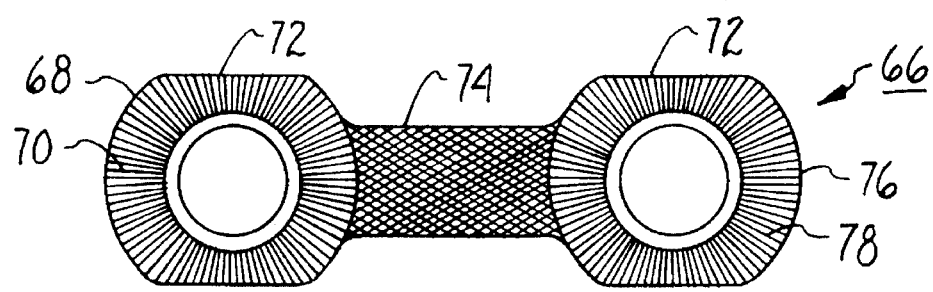
FIG. 16a is a plan view of a length variation on the bridge plate preferred embodiment of the bridge assembly.

Referring to FIG. 16a, there is seen a schematic plan view of a variation on the bridge plate 66 preferred embodiment of the bridge assembly 22 (FIG. 5a). The bridge plate 66 is about 1.6 inches in length and about 0.152 inches in thickness. The bridge plate 66 is also of titanium alloy Ti6A14v.

This bridge plate 66 consists of a first end 68 and a second end 76 connected by a connecting piece 74. Both first end 68 and second end 76 have a radially extended serrated lower surface 70.

The first end 68 and said second end 76 have an angular rotation spacer 58 (FIG. 11a) which matches the surface serration pattern on these ends 68 and 76, and is physically attached to the eyebolt assembly 32 (FIG. 4) with a bridge assembly hex nut 38 (FIG. 5a).

The bridge plate 66 is overall surface treated with an interstitial process to prevent galling and fretting.

The bridge plate 66 has variable dimensions, as needed, to properly span between one rod 20 (FIG. 14) and another essentially parallel rod 20. The rods 20 are also separated dimensionally, depending on their application.

Figure 16B:
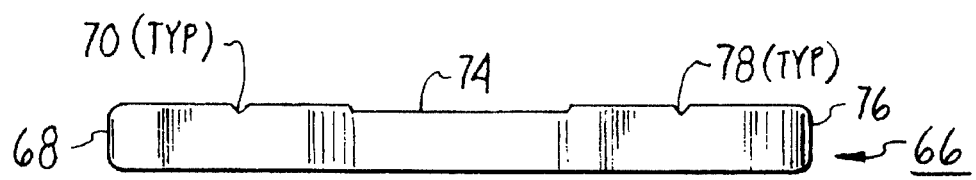
FIG. 16b is a front view of a length variation on the bridge plate preferred embodiment of the bridge assembly

Referring next to FIG. 16b, there is seen a schematic front view of a variation on the bridge plate 66 preferred embodiment of bridge assembly 22 (FIG. 5a).

Figure 17A:
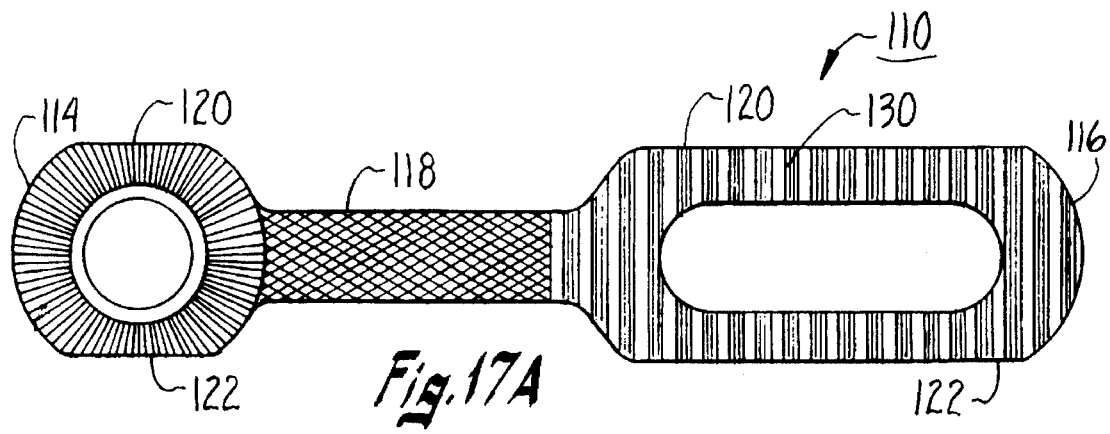
FIG. 17a is a plan view of a length variation on the modular bridge second embodiment of the bridge assembly.

Referring now to FIG. 17a, there is seen a schematic plan view of a variation on the modular bridge 110 second embodiment of the bridge assembly 22 (FIG. 5a).

The modular bridge 110 construction is about 2.175 inches in overall length and about 0.152 inches in thickness.

This modular bridge 110 has variable dimensions, as needed, to properly span transversely the parallel rods 20, just as does the bridge plate 66 embodiment. This modular bridge is also of titanium alloy Ti6A14V.

The modular bridge 110 has a modular first end 114 and a modular second end 116. The first end 114 is integrally connected to the second end 116 through an elongated, essentially flat metallic crosshatched piece 118.

The first end 114 is of an essentially circular doughnut shape, of inner diameter of approximately 0.25 inches. The outer diameter is approximately 0.60 inches. The modular top 120 and modular bottom 122 are flattened as shown.

The second end 116 is of an essentially elongated rectangular shape, holed in the center, leaving a metallic border surrounding the center. This rectangular shape feature is key to allowing lateral or transverse adjustment of the modular bridge 110 to accommodate different require spans between the rods 20. The inner radius is about 0.125 inches. Distance between centers is about 0.50 inches, while the outer width is about 0.475 inches. The second top 124 and second bottom 126 of this second end 116 are also flattened.

The modular first end 114 has a modular radially extended serrated lower surface 122, and the modular second end 116 has a modular lateral serrated lower surface 130. This modular bridge 110 is also overall surface treated to prevent galling and fretting.

Figure 17B:
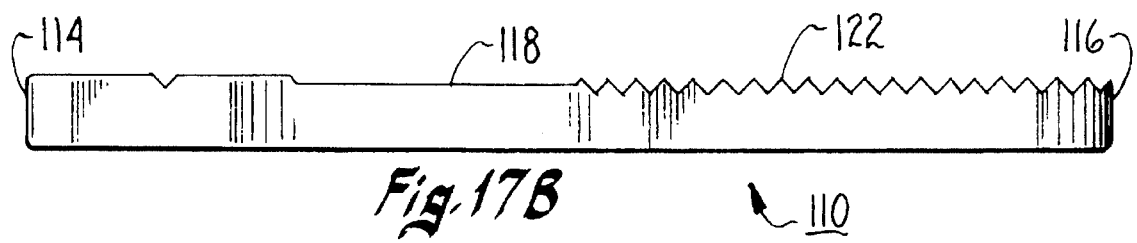
FIG. 17b is a front view of a length variation on the modular bridge preferred embodiment of the bridge assembly.

Referring to FIG. 17b, there is seen a schematic front view of a variation on the modular bridge 110 embodiment of the bridge assembly 22 (FIG. 5a).

Referring next to FIG. 18a, there is seen a schematic plane view of a variation on the height adjustment spacer used with bone screw 28 (FIG. 6c). This variation is the modular spacer bridge or adapter 132 used with the modular bridge 110 (FIG. 17b) embodiment of the bridge assembly 22. The lateral serrated upper surface 136 is also seen.

Referring now to FIG. 18b, there is seen a schematic front view of the modular spacer bridge or adapter 132. The lateral serrated upper surface 136 meshes with the lateral serrated lower surface 130 of the modular bridge 110 (FIG. 17b).

Referring to FIG. 18c, there is seen a schematic underside view of the modular spacer-bridge or adapter 132. This view shows the flush grooved lower surface of the modular spacer bridge or adapter 132 that conforms to one of the essentially parallel rods 20 (FIG. 14).

(Note that the modular spacer bridge also has a modular spacer top 138 and modular spacer bottom 140. Both top 138 and bottom 140 are flattened.)

Referring next to FIG. 19a, there is seen a schematic plan view of the low profile bridge 112, third embodiment of the bridge assembly 22 (FIG. 5a). This low profile bridge 112 is about 1.148 inches in overall length and about 0.152 inches in thickness. The low profile bridge 112 has variable dimensions, as needed, to properly span transversely the parallel rods 20 (FIG. 14). The low profile bridge is also of titanium alloy Ti6A14V.

The low profile bridge 112 is I beam shaped when viewed from a position above. It has four arms 142 of identical dimensions projecting from a center web 144. These arms 142 bend downward to approximate the general shape of a horseshoe when viewed from the front or rear.

Referring now to FIG. 19b, there is seen a schematic front view of a variation on the low profile bridge 112 third embodiment of the bridge assembly 22 (FIG. 5a).

Referring to FIG. 19c, there is seen a schematic side elevation view of a variation on the low profile bridge 112. Note that top-LP 146 and bottom-LP 148 are flattened.

Referring finally to FIG. 20, there is seen a block diagram illustrating the method of installing a spinal fixation system 10 shown in FIG. 1.

The first step, as indicated in box 200 is exposing the patient's spinal column through surgery procedures.

The second step, as indicated in box 202 is inserting bone screws or hooks into the pedicle region of the vertebral body. The bone screw is also used in the sacrum.

The third step as indicated in box 204 is slipping modified forceps into the female slots on the slot side surface of each of the bone screws, as needed.

Male probes slip easily into the self-aligning female slots on the sides of the yoke rather than the surgeon having to hunt for multiple small holes as used in same devices.

The next step as indicated in box 206 is hooking hooks around laminar and other bone structure as needed.

The next step as indicated in box 208 is bending one or more rods of titanium alloy Ti6A14V conforming to the various curves of the pedicle area of the spinal column.

A flexible and malleable metallic rod is then placed into the area of the vertebral body oriented parallel to the vertebrae. Preferably and typically, there are two parallel rods used in any of these constructs.

The next step as indicated in box 210 is assembling the eyebolt assemblies.

The next step, as indicated in box 212 is sliding eyebolt assemblies onto the rods.

The next step, as in indicated in box 214 is positioning the eyebolt assemblies in the immediate vicinity of the bone screw.

The next step, as indicated in box 216 is using modified forceps to adjust height and angular orientation of the bone screws to attach to the eyebolt assembly with the rod.

The next step, as indicated in box 218 is attaching the eyebolt assemblies to the elongated yoke of the bone screw.

An eyebolt assembly is next placed over each of the rods, then slipped along the rod to the area of each of the bone screws and hooks which were previously positioned. Prior to use, when using bone screws, this eyebolt assembly comes partially assembled with an eyebolt onto which is loosely placed an angular rotation spacer and a height adjustment spacer with positioning tabs. An eyebolt restraint hex nut has already been placed over the angular rotation spacer, but prevented from falling off the bolt portion of the eyebolt by staking the bolt end. At this point, the eyebolt assembly and rod are joined together. The two are lowered by the surgeon onto the bone screw so that the bolt portion of the eyebolt assembly slips into the yoke of the bone screw. The positioning tabs on the height adjustment spacer are used to guide this spacer around the yoke of the bone screw. These tabs ensure that the parallel serrated inner surface of the yoke meshes with the parallel serrated outer surface of the height adjustment spacer. The surgeon then can refine the height of the bolt portion of the eyebolt by observation. The eyebolt restraint hex nut is then tightened with a surgical wrench to the proper torque.

The last step, as indicated in box 220 is installing the bridge assembly between adjacent eyebolt assemblies located on the essentially parallel rods, for maintaining the stability and strength to the spinal fixation system within an animal or human object. The bridge assemblies include optionally one or more of three types of bridge assemblies: bridge plate, modular bridge or low profile bridge, one or more of the angular rotation spacers as needed, one of the modular spacer bridge providing lateral adjustments, and an appropriately sized bridge assembly restraint hex nut.

At this point, the surgeon needs to add strength and stability to the construct. Angular rotation movement is possible by using an angular rotation spacer between the eyebolt and the bridge assembly. Width adjustment can be achieved by using a spacer with a transverse or lateral serrated upper surface. Several different sizes of components can be used. The restraint nut is tightened with the proper torque and using the proper surgical wrench after the construct is completed assembly.

The modular bridge is particularly useful in the lower lumbar area when a greater transverse span between essentially parallel rods exists. The low profile bridge is particularly useful when the surgeon has a more restricted body cavity space and needs a minimum of height. In addition, this low profile bridge embodiment would minimize the altered profile of the patient after surgery. Sometimes the hardware profile can be seen or felt.

It can be seen that the present invention provides a novel apparatus and method which provides a breakthrough in applying the concepts of skeletal fixation systems.

The foregoing description of the present invention is explanatory thereof and various changes in the size, or shape, as well as on the details of the illustrated construction may be made, within the scope of appended claims without departing from the spirit of the invention.

What is claimed is:

1. A spinal fixation apparatus, comprising:

a plurality of eye bolt assemblies, each comprising an eye bolt having an eye adapted to receive a rod;

at least two generally parallel rods, each extending through the eye of an eyebolt a spinal attachment member connected to each rod;

a bridge having a first end and a second end spanning said rods, wherein said first end and said second end have a first hole and a second hole therethrough, respectively, wherein a surface of said bridge proximate said first hole defines a plurality of serrations extending radially about said hole, and wherein a surface of said bridge proximate said second hole defines a plurality of parallel serrations; and first and second adapters, said first adapter engaging one of said eyebolts and said first end of said bridge and said second adapter engaging another of said eyebolts and said second end of said bridge.

2. The apparatus according to claim 1, wherein said bridge is between about 0.1 and 0.2 inches thick.

3. The apparatus according to claim 1, wherein said bridge is made of titanium alloy Ti6A14V.

4. The apparatus of claim 1 wherein said apparatus further comprises an adapter positioned between the first end of said bridge and said eyebolt, said adapter having radial serrations on one surface so that the bridge can mount to said eyebolt in varying angular orientations with respect to said rod.

5. The apparatus of claim 1 wherein said second adapter has lateral serrations on one surface so that the bridge can mount to the eyebolt in varying lateral positions with respect to said rod.

6. The apparatus of claim 1 wherein said spinal attachment member is a bone screw.

* * * * *